United States Patent [19]
Harris et al.

[11] Patent Number: 5,441,987
[45] Date of Patent: Aug. 15, 1995

[54] ANTIFUNGAL AGENT

[75] Inventors: Guy H. Harris, Cranford; James E. Curotto, Morgan; Robert A. Giacobbe, Lavallette; Suzanne M. Mandala, Scotch Plains; Richard L. Monaghan, Morristown, all of N.J.; Richard K. Jansson, Doylestown, Pa.; Joan A. Lasota, Ringoes, N.J.

[73] Assignee: Merck & Co., Inc., Rahway, N.J.

[21] Appl. No.: 289,863

[22] Filed: Aug. 12, 1994

[51] Int. Cl.⁶ .............................................. A61K 31/12
[52] U.S. Cl. .................................... 514/691; 435/148; 435/254.1; 568/374
[58] Field of Search .................. 568/374; 514/691; 435/148; 71/122

[56] References Cited
U.S. PATENT DOCUMENTS 5,276,055 1/1994 Cabello et al. ........................ 514/546
5,304,487 4/1994 Bills et al. ........................... 435/254.1

Primary Examiner—James H. Reamer
Attorney, Agent, or Firm—Elliott Korsen; Mark R. Daniel

[57] ABSTRACT

A compound having the formula

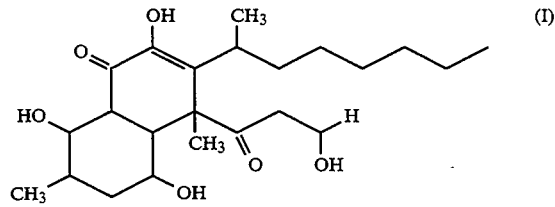

which is useful as an antifungal agent and for the treatment and control of several agricultural phytopathogens, including *Phytophthora infestans*, is disclosed.

10 Claims, 1 Drawing Sheet

ANTIFUNGAL AGENT

DISCLOSURE OF THE INVENTION

The present invention is directed to a compound of the formula

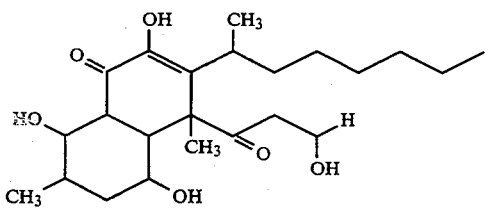

The compound has antimicrobial and fungicidal properties. Additionally, it is contemplated that the compound may be effective as a broad spectrum crop antifungal agent. In particular, the compound may be useful against agricultural *Phytophthora infestans* infections which are found as blight on tomato and potato plants. The compound may also be useful for controlling fungal infections in humans.

The compound is obtained by the cultivation of *Sporormiella australis*. *Sporormiella australis* is the subject of U.S. Pat. No. 5,304,485 issued Apr. 19, 1994.

Figure 1:
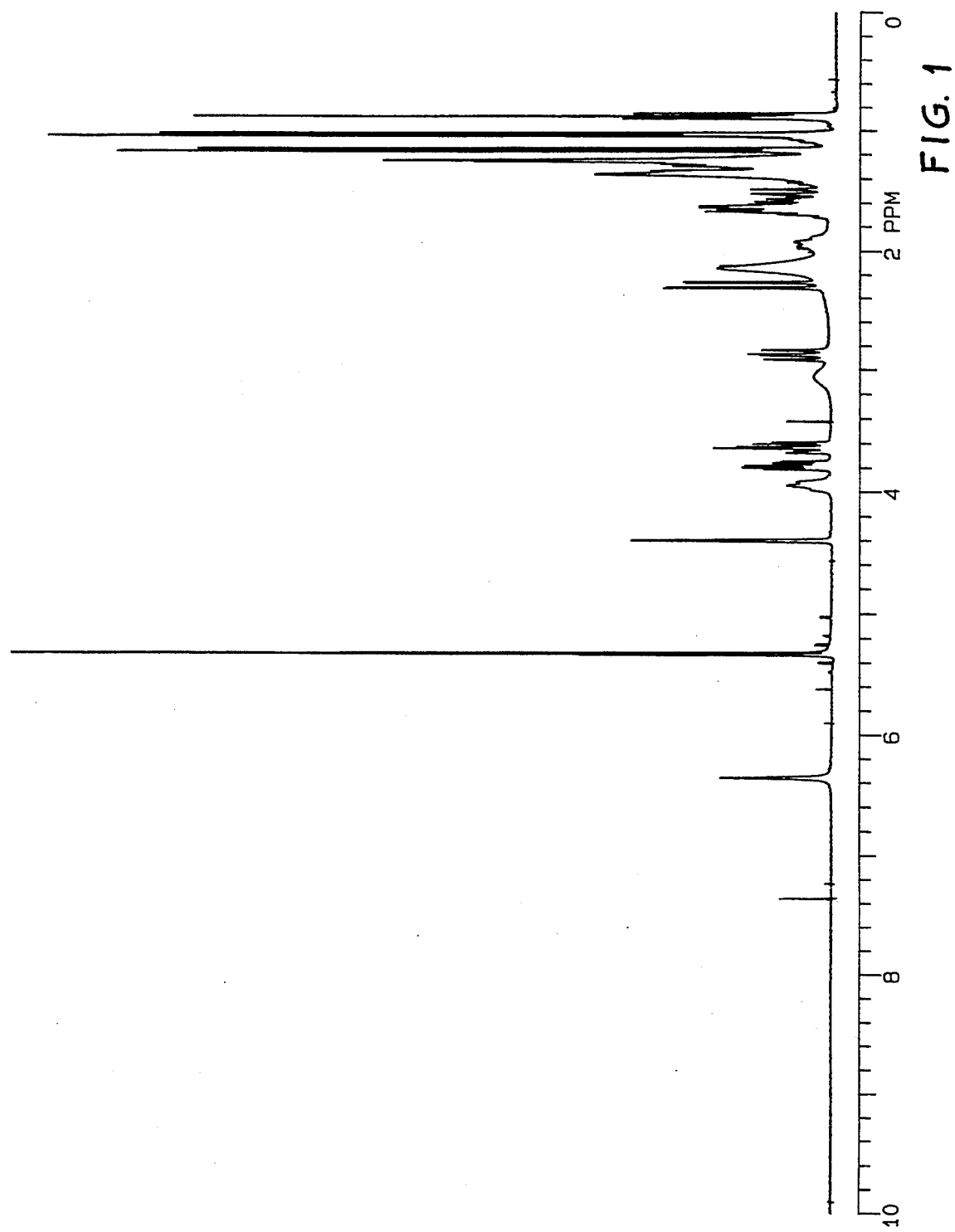
FIG. 1 is a proton nuclear magnetic resonance spectrum for Compound I. The peak shown at approximately 5.3 ppm represents the solvent, $CD_2Cl_2$.

The compounds are light-colored solids characterized by the following spectral properties.

ULTRAVIOLET SPECTRAL DATA

At 25 μg/ml in $CH_3OH \lambda_{max}$: 275 mm ($\epsilon$=11,600)

INFRARED SPECTRAL DATA as a thin film on ZnSe crystal, 2958, 2932, 1698, 1666, 1635, 1397, 1041 cm$^{-1}$.

NMR SPECTRAL DATA

$^{13}C$ NMR Spectra

The $^{13}C$ NMR spectra of Compound I was recorded in $CD_2Cl_2$ at 75 MHz on a Varian XL-300 spectrometer at ambient and at low temperature. Because of exchange broadening processes at ambient temperature, several resonances in Compound I were severly broadened.

Chemical shifts are given in ppm relative to tetramethylsilane (TMS) at zero ppm using the solvent peak at 53.8 ppm as internal standard.

$^{13}C$ NMR shifts of Compound I (20 mg in 0.7 ml $CD_2Cl_2$; 20° C.): 14.2, 14.7, 17.5, 17.7, 23.0, 28.8, 29.8, 32.2, 34.3* (2), 36.0*, 37.3, 48.1, approx. 56*, 59.5*, 68.4, 70.8, approx. 140*, 145.4*, 193.2, approx. 213*. Resonances marked with (*) severely broadened. Only 21 of 23 carbons observed.

$^{13}C$ NMR Shifts of Compound I (20 mg in 0.7 ml $CD_2Cl_2$; −42° C.): 14.1 (2, q), 17.0 (q), 17.5 (q), 22.8 (t), 28.7 (t), 29.5 (t), 31.9 (t), 33.7 (d), 34.1 (t), 35.5 (d), 36.9 (t), 39.8 (d), 41.4 (t), 47.4 (d), 55.5 (s), 60.1 (t), 68.7 (d), 69.7 (d), 139.1 (s), 145.1, 192.5 (s), 212.0 (s). The carbon count of 23 is in agreement with the molecular formula of $C_{23}H_{38}O_6$ derived by HRMS.

$^1H$ NMR Spectra

The $^1H$ NMR spectra of Compound I is seen in FIG. 1. The spectra was recorded in $CD_2Cl_2$ at 300 MHz on a Varian XL-300 spectrometer at ambient and at low temperature. Chemical shifts are given in ppm relative to TMS at zero ppm using the internal solvent peak at 5.32 ppm as the internal standard.

The compound of this invention has antimicrobial properties. It is especially useful as an antifungal agent against both filamentous fungi and yeasts. It is useful against organisms causing pathogenic mycotic infections such as *Candida albicans, Candida guilliermondii, Candida parapsilosis, Cryptococcus neoformans, Candida pseudotropicalis, Candida tropicalis, Saccharomyces cerevisiae, Aspergillus flavus, Aspergillus fumigatus* and the like. The properties may be effectively utilized by administering compositions containing an antifungal amount of Compound I to an area, object or subject, on or in which fungi are to be controlled. Thus, compositions containing an antifungally effective amount of Compound I and their use for the control of fungi are aspects of the present invention. An especially preferred aspect of the present invention are compositions in a pharmaceutically acceptable carrier and their use for the control of mycotic infections by administering a therapeutically effective amount of the compound. Antimicrobial properties embrace activity against bacteria, particularly Bacilli. However, the most highly useful antimicrobial activity is that: of Compound I against fungi.

The compound of this invention also has agricultural antifungal properties. The compound can be used both to treat and control phytopathogens. When the term control is used, it is intended to imply both prophylactic use and preventive use of the compound. Compound I is especially useful as an antifungal agent against Oomycete fungi on plants, including potato late blight, *Phytophthora infestans*, and downy mildew of grape, *Plasmopara viticola*. It is also useful as an antifungal agent for control of Deuteromycete fungi such as early blight, *Alternaria solani* and grey mold, *Botrytis cinerea* and Basidiomycete fungi such as wheat leaf rust, *Puccinia recondita*. These properties may be utilized by administering compositions containing an antifungal amount of the compound to an area, object or subject, on or in which fungi am to be controlled.

The compound of the present invention is a natural product and is conveniently produced by the cultivation of *Sporormiella australis* MF 5672 in the culture collection of Merck & Co., Rahway, N.J. and which has been deposited under the Budapest Treaty in the culture collection of the American Type Culture Collection at 12301 Parklawn Drive, Rockville, Md. 20852, and assigned accession number, ATCC 74157.

The fungus which was isolated from moose dung and identified as *Sporormiella australis* has colonial and morphological properties as follows:

Colonies on oatmeal agar (Difco) at 20° C., 95% relative humidity, 12 hour photoperiod under fluorescent light, attaining 34–37 mm in 14 days, appressed to felty of sparsely floccose at the center, with margin even and submerged, dry, dull, pale gray to dark olivaceous gray, Pale Smoke Gray, Deep Grayish Olive, Iron Gray, Dark Olive-Black (capitalized color names from Ridgway, R. 1912. *Color Standards and Nomenclature*, Washington, D.C.), often developing conspicuous lightly pigmented sectors that originate from inoculum source, with sectors pale olivaceous yellow to pinkish olive, Avellaneous, Deep Olive Buff, reverse dull olivaceous gray to gray, pinkish gray or yellow in the sectors. Exudates and odors absent.

Colonies on malt extract agar (Difco), same conditions, attaining 26–28 mm in 14 days, appressed to felty, becoming sparsely floccose, dry, dull, with margin even, submerged, white, pale gray to dull olivaceous gray, Pale Smoke Gray, Smoke Gray, Grayish Olive, developing unpigmented sectors, reverse dark gray to nearly black, with yellow to grayish sectors. Exudates and odors absent.

Colonies on cornmeal agar (Difco), same conditions, attaining 8–12 mm in 14 days, similar in color and appearance to colonies on malt yeast extract agar, but more translucent.

Colonies of this strain, as well as those of other *Sporormiella spp.*, have a strong tendency to develop aberrant and attenuated sectors, especially after repeated transfer. These sectors are generally paler in color and have lost or have reduced their ability to differentiate stromata and/or pseudothecia.

Ascoma a pseudothecium. Pseudothecia evident in 10–21 days, maturing in 4–5 weeks on oatmeal agar. Pseudothecia single, densely gregarious, or confluent, embedded, with the upper 10–60% protruding above the surface, 100–400 μm in diameter, globose to subglobose, with a minute apical papilla, non-ostiolate, glabrous, dull, black. In culture, pseudothecia often become moribund and fail to fully mature within 4–8 weeks. Often development is arrested with only the formation of asci initials and paraphyses. Peridium thin, 1–3 cells thick, a textura angularis. Peridial cells isodiametric, 3–8 μm in diameter, gray to dark olivaceous gray in KOH. Asci abundant, arising from the base of the psuedothecial cavity, bitunicate, 8-spored, cylindrical, straight to slightly curved, with broad rounded apex, 110–160 X 15–21 μm, tapering abruptly at the base into a short stalk, with basal stalk 5–10 μm long. Paraphyses abundant, interspersed among asci; filamentous, 1–3 μm wide, septate, approximately equal in length with asci. Ascospores biseriate within the ascus, 32–42 X 6–9 μm, 4-celled, constricted at the septa, with terminal cells with rounded apices; central cells cylindrical to doliform, each cell with an thin, faint lateral germ slit, with entire ascospore surrounded by a thin, refractive, hyaline sheath, with cells often separating when removed from ascus, dark olivaceous or brownish gray in KOH.

The production of Compound I may be carried out by cultivating *Sporormiella australis* ATCC 74 157 in a suitable nutrient medium under conditions hereinafter described until a substantial amount of antifungal activity is detected in the fermentation broth, harvesting by extracting the active components from the mycelial growth with a suitable solvent, concentrating the solution containing the desired component, then subjecting the concentrated material to chromatographic separation to isolate Compound I from the other metabolites also present in the cultivation medium.

Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extract, corn steep liquors, distillers solubles, cottonseed meal, meat extract, and the like. The various sources of nitrogen can be used alone or in combination in amounts ranging from 0.05 to 5 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included is a representative seed medium.

TABLE 1

KF SEED MEDIUM

| Component | per liter | Trace Element Mix | per Liter |
|---|---|---|---|
| Corn Steep Liquor | 5 g | $FeSO_4.7H_2O$ | 1 g |
| Tomato Paste | 40 g | $MnSO_4.4H_2O$ | 1 g |
| Oat Flour | 10 g | $CuCl_2.2H_2O$ | 25 mg |
| Glucose | 10 g | $CaCl_2$ | 100 mg |
| Trace Element Mix | 10 ml | $H_3BO_3$ | 56 mg |
| | | $(NH_4)_6Mo_7O_{24}.4H_2O$ | 19 mg |
| | | $ZnSO_4.7H_2O$ | 200 mg | pH = 6.8

TABLE 2

SOLID FERMENTATION MEDIUM
Production Medium F1

| Component | Amount (per 250-ml flask) |
|---|---|
| Cracked Corn | 10.0 g |
| Ardamine PH | 2.0 mg |
| $KH_2PO_4$ | 1.0 mg |
| $MgSO_4.7H_2O$ | 1.0 mg |
| Na Tartrate | 1.0 mg |
| $FeSO_4.7H_2O$ | 0.1 mg |
| $ZnSO_4.7H_2O$ | 0.1 mg |
| Distilled Water | 10.0 ml | no pH adjustment

TABLE 3

LIQUID MEDIUM
Medium MOF

| Component | Amount (per liter) |
|---|---|
| D-Mannitol | 75.0 g |
| Oat Flour | 15.0 g |
| Fidco Yeast Extract | 5.0 g |
| L-Glutamic Acid | 4.0 g |
| MES* | 16.2 g |
| Distilled Water | 1000 ml | pH adjusted to 6.0 with NaOH
*[2-(N-morpholino)ethanesulfonic acid] monohydrate (MES)

TABLE 4

LIQUID MEDIUM
Medium RG122

| Component | (per liter) |
| --- | --- |
| D-Mannitol | 91.0 g |
| Corn Steep Liquor | 4.0 ml |
| Lard Water | 4.0 g |
| Pectin | 10.0 g |
| KH$_2$PO$_4$ | 4.0 g |
| Tomato Paste | 4.0 g |
| Serine | 10.0 g |
| Peptonized Milk | 4.0 g |
| Peanut Meal | 4.0 g |
| Distilled Water | 1000 ml | pH adjusted to 7.0 with NaOH

TABLE 5

LIQUID MEDIUM
Medium KRC

| Component | Amount (per liter) |
| --- | --- |
| Dextrin (starch) | 40.0 g |
| Distiller Solubles | 7.0 g |
| Yeast Extract | 5.0 g |
| CoCl$_2$6H$_2$O | 50.0 mg |
| Beta Cyclodextrin | 10.0 g |
| Distilled Water | 1000 ml | pH adjusted to 7.3 with NaOH

Of the foregoing media, the solid medium, F1, was found to give the best yield of Compound I. Generally, in the production of the desired compound, the culture is first grown in a seed medium and the culture growth then used to inoculate a production medium. The production medium may be a solid medium or a liquid medium.

In carrying out the production of Compound I, frozen mycelia of culture *Sporormiella australis* MF 5672, ATCC 74157 is inoculated into nutrient seed medium at a pH in the range of 5 to 8, preferably pH 7, such as that in Table 1 (KF Seed Medium). The seed flasks are then incubated with agitation at temperatures in the range of from about 15° C. to about 30° C., preferably about 25° C., for a period of from about 2 to 15 days, preferably 3 to 5 days at about 50% relative humidity. When the growth is abundant, usually between 3 to 5 days, the growth may be used to inoculate the production medium for the production of Compound I.

If appropriate, a second stage fermentation may be carded out in the seed medium for greater production of mycelial mass by inoculating fresh seed medium with a portion of the culture growth and then incubating under similar conditions but for a shortened period. The resulting growth then may be employed to inoculate the production medium which may be solid but is preferably liquid.

When the production is carried out on solid medium, a portion of the seed is used to inoculate the solid medium in a conventional manner and the resulting medium incubated under static conditions preferably at 25° C. and 50 percent relative humidity for 7 to 25 days, preferably 11 to 14 days.

After completion of the cultivation period, as can be determined by HPLC or TLC of the fermentation broth, the product is recovered and thereafter isolated. The secondary metabolites may be extracted from the mycelial growth by shaking at 220 rpm for one hour at 25° C. with either 50 percent aqueous methanol, methanol, ethyl acetate, methyl ethyl ketone or butanol acidified with 0.2 percent trifluoroacetic acid. The mixture is then filtered to remove the solid and to obtain the product in the tiltrate. The tiltrate is concentrated under reduced pressure to obtain the crude product as residue.

When the fermentation is carried out in a liquid medium, a portion of the seed is used to inoculate the liquid medium in a conventional manner and the resulting medium incubated with agitation, preferably at 25° C. and 50% relative humidity for from 4 to 25 days, preferably 11 to 14 days.

The fermentation broth is acidified to pH 3.0 with sulfuric acid, then an equal volume of ethyl acetate or methyl ethyl ketone is added and the resulting mixture shaken at 220 rpm for 1 hour at 25° C. The organic solvent is removed and the remaining mycelium aqueous phase is reextracted several more times, and the extracts combined and the combined extracts subjected to reduced pressure to obtain Compound I as residue. Other suitable extraction solvents include ethyl acetate, butanol acidified with 0.2 percent trifluoroacetic acid, acetone and methanol.

The product residue from either solid or liquid fermentation is isolated by chromatography, preferably on silica gel, but also may be on silica based reverse phase, dextran gel, and the like.

In carrying out the isolation, the extract is concentrated to obtain an oil containing product which is then partitioned between a non-polar hydrocarbon and polar alcohol to remove non-polar impurities. Preferred solvents for partitioning are hexanes and methanol. The alcohol extract is concentrated to dryness to obtain crude product which may be purified employing silica gel chromatography and using hexane/ethyl acetate/acetic acid as eluant. The appropriate fractions are then pooled, concentrated and further purified.

The preferred method for final purification of Compound I is reverse phase chromatography. The stationary phase may be either a $C_8$ or $C_{18}$ bonded phase. The preferred eluant for the reverse phase chromatography of Compound I is a buffered mixture of water and either acetonitrile or methanol. Compound I may then be recovered by extraction into an immiscible organic solvent such as ethyl acetate.

The usefulness of Compound I as an antifungal agent, especially as an antimycotic agent may be demonstrated with Compound I in a broth microdilution assay for the determination of minimum inhibitory concentration (MIC) and minimum fungicidal concentration (MFC) against fungi. In such assay against a panel of fungi selected for their resistance/susceptibility to known compounds, animal virulence, source and clinical importance, Compound I is found to have activity.

In the microbroth dilution assay, microorganisms were selected by streaking a yeast culture on Sabouraud dextrose agar (SDA) incubating for 24–48 hours at 35°–37° C., thereafter selected 3 to 5 characteristic colonies and transferring to a fresh plate and incubating under similar conditions. From the regrowth, 3 to 5 colonies were selected and suspended in 10 milliliters of YM broth (Difco) and incubated for 4 hours at 35°–37° C. shaking at 225 rpm. The 4 hour broth cultures were adjusted optically to 86% transmission resulting in a concentration of 1–5 × $10^6$ cfu/ml which was further diluted 1:100 in YNBD (yeast nitrogen base with 1% dextrose) to obtain a concentration of 1–5 × $10^4$ cfu/ml for use as inocula.

The test compound, Compound I, and control compounds were prepared as stock solutions of 512 μg/ml in 10% DMSO and 75 μl of said solution delivered to each well in column 1 of a 96-well, U-bottomed microtiter plate. The compounds in column 1 were then serially diluted two-fold to yield concentrations from 128 μg/ml to 0.6 μg/ml.

The plates containing the diluted compounds were then inoculated with 75 μl/well of the appropriate microorganism and incubated for 48 hours at 35°-37° C. with MIC (minimum inhibitory concentration) determinations carried out after 24 hours of incubation. Growth and sterility controls for each organism and sterility checks for the compounds also were carried out.

After recording MICs at 24 hours, the microtiter plates were shaken gently to resuspend the cells. A 1.5 μl sample was transferred from each well of the 96-well microtiter plate to a single reservoir inoculum plate containing SDA. The inoculated SDA and corresponding microtiter plates were incubated for 24 hours at 35°-37° C. For *Cryptococus neoformans*, SDA plates were inoculated at 48 hours after recording MICs and incubated 48 hours before reading the MFC. MFC is the lowest concentration of compound at which either no growth or growth of ≦4 colonies occur.

*In Vitro* Minimum Inhibitory Concentration (MIC) and Minimum Fungicidal Concentration (MFC) (μg/ml)

| Strain | Compound MIC | Compound MFC | Control* MIC | Control* MFC |
| --- | --- | --- | --- | --- |
| Candids albicans (MY 1028) | 32 | 32 | 2 | 2 |
| C. albicans (MY 1750) | 64 | 32 | 2 | 2 |
| C. guillermondii (MY 1019) | 16 | 16 | 2 | 4 |
| C. parapsilosis (MY 1010) | 64 | 64 | 2 | 2 |
| C. pseudotropicalis (MY 2099) | 16 | 32 | 4 | 4 |
| C. tropicalis (MY 1012) | 32 | 32 | 64 | 32 |
| Cryptococcus neoformans (MY 1051) | 8 | 16 | 2 | 4 |
| C. neoformans (MY 1146) | 32 | 32 | 2 | 2 |
| C. neoformans (MY 2061) | 16 | 16 | 2 | 2 |
| C. neoformans (MY 2062) | 16 | 32 | 2 | 2 |
| Saccharomyces cerevisiae (MY 1976) | 16 | 16 | 1 | |
| Aspergillus fumigatus (MF 4839) | 32 | | 4 | |
| A. fumigatus (5668) | 32 | | 4 | |
| A. fumigatus (5669) | 32 | | 4 | |

*Amphotericin B

Compound I is also useful as a broad spectrum antifungal agent for agricultural use as shown in an in vivo assay using various phytopathogens. In the assay, a panel of seven pathogens: late blight, *Phytophthora infestans*, on tomato; early blight, *Alternaria solani*, on tomato; downy mildew, *Plasmopara viticola*, on grape;, grey mold, *Botrytis cinerea*, on pepper; glume blotch, *Septoria nodorum*, on wheat; wheat leaf rust, *Puccinia recondita*, on wheat; and powdery mildew of wheat, *Erysiphe graminis;* were challenged with different concentrations of Compound I in a protectant assay.

Compound I was compared with established agricultural antifungal agents, metalaxyl or propiconazole. Test plants are sprayed to runoff with different concentrations of the test materials and then inoculated after spray material had dried with each of the seven pathogens. After inoculation, plants were placed in one of three controlled environment rooms set at either 18° C., 22° C. or 24° C. Non treated plants inoculated with each pathogen were used as control. Plants were rated visually for percent control of each pathogen. Plants inoculated with *P. infestans*, *A. solani* and *B. cinerea* were evaluated after four days; plants inoculated with *S. nodorum* were evaluated after 10 days; plants inoculated with *P. viticola* were evaluated after 12 days; and plants inoculated with *P. recondita* and *E. graminis* were evaluated after 10-14 days. Compond I was most efficacious at controlling Oomycete fungi on plants and resulted in up to 90% control of *Phytophthora infestans* and 85% control of *Plasmopara viticola* when tested at a concentration fo 50 ppm.. Moderate control of *Alternaria solania*, *Botrytis cinerea* and *Puccinia recondita* was also observed at 50 ppm.

Compound I is also useful for inhibiting the growth of filamentous fungi. Such use may be illustrated in the following tests with *Aspergillus fumigatus*, *Aspergillus niger*, *Aspergillus flavus*, *Fusarium oxysporum*, *Rhizomicor miehei*, *Ustilago zeae* and the like.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

The samples to be tested for production of antifungal agent are applied to 6.2 mm. filter paper discs (25 microliter/disc) and air dried at 24° C. When the sample to be tested is crude broth, it may be centrifuged prior to application. The discs bearing the material to be tested are then applied employing sterile conditions to the seeded assay plates and the samples rewet with 25 percent sterile aqueous dimethylsulfoxide (25 μl/disc). The assay plates are then incubated at either 28° C. or 37° C. for 24 hours. Following incubation, the inhibition zones are measured. Growths are also noted as to appearance. Compound I is seen to effectively inhibit growth of the fungal organisms.

The compounds also have antimicrobial activity against bacteria. Thus, in an assay carried out in a manner similar to that above-described for filamentous fungi, zones of inhibition are noted when *Bacillus subtilis* is a test organism.

The following example illustrates the invention but is not to be construed as limiting:

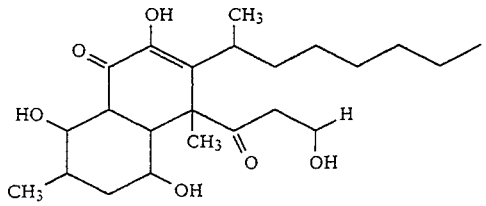

A frozen vegetative mycelia of *Sporormiella australis* MF 5672 in the culture collection of Merck & Co., in Rahway, N.J. was inoculated into 54 milliliters of KF seed medium (Table 1 ) in a 250 milliliter unbaffled Erlenmeyer flask. The seed flasks were incubated for three days at 25° C. and 50 percent relative humidity on a rotary shaker with a 5-cm throw at 220 rpm.

Two milliliter portions of the 3-day culture growth were used to inoculate a fermentation production medium, Medium MOF, contained in eighty 250 milliliter flasks and the inoculated media incubated under static conditions at 25° C. and 50 percent relative humidity for 11 days.

After 11 days, 50 milliliters of ethyl acetate was added to each flask and the mixture agitated at 220 rpm for 2 hours at room temperature and thereafter filtered through a celite pad to obtain 25.3 grams of ethyl acetate extract.

The extract was concentrated in vacuo to an oil (78 ml) which was partitioned between 270 ml of methanol and 360 ml of hexane. The methanol layer was removed and extracted two additional times with 350 ml hexane. The methanol layer was concentrated in vacuo to an oil and dissolved to a final volume of 14.4 ml in ethyl acetate. A 14.0 ml portion was loaded onto a 750 ml silica gel column which had been dry packed and equilibrated with a solution of 60 parts hexane/40 parts ethyl acetate/1 part glacial acetic acid. The column was washed with 2150 ml of the solution at 15 ml/min. The column was then eluted with a solution of ethyl acetate containing 1% (v/v) glacial acetic acid at 15 ml/min. collecting 1.5 minute (22.5 ml) fractions. Fractions 21–40 were pooled and concentrated in vacuo to yield 1.79 g of crude Compound I.

The crude Compound I (100 mg) was further purified in two identical runs by preparative HPLC on Whatman Partisil 10 ODS (25 cm×22 mm dia.). The column was eluted at a flow rate of 15 ml/min. with 45% acetonitrile/55% aqueous 0.025 M $KH_2PO_4$, pH 6.8, collecting 0.5 min. fractions. Fractions 30 to 32 were pooled, adjusted to pH 3.0 and the solution extracted with and equal volume of ethyl acetate. The ethyl acetate layer was washed with an equal volume of water, then one half volume of aqueous NaCl and dried over anhydrous $Na_2SO_4$. Filtration and concentration of the ethyl acetate layer yielded 88 mg of Compound I.

Physiochemical Chracteristics of Compound I

HREI-MS: Found 410.2613, Calc. for $C_{23}H_{38}O_6$ 410.2668

Optical Rotation: +98° ($CH_3OH$, c 0.99)

Compound I had the spectral properties previously described.

EXAMPLE II 1000 compressed tablets each containing 500 milligrams of Compound I are prepared from the following formulation:

|  | Grams |
| --- | --- |
| Compound I | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE III 1000 hard gelatin capsules, each containing 500 milligrams of Compound I are prepared from the following formulation:

| Compound | Grams |
| --- | --- |
| Compound I | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE IV 250 milliliters of an injectable solution are prepared by conventional procedures from the following formulation:

| Dextrose | 12.5 grams |
| --- | --- |
| Water | 250 milliliters |
| Compound I | 400 milligrams |

The ingredients are blended and thereafter sterilized for use.

Isolation of *Sporormiella australis*

A sample of moose dung was first thoroughly washed with tap water, and about 0.75 gram of the sample were then homogenized in a blender and resuspended in 150 milliliters of sterile distilled water. A 1:10 dilution was made from this suspension, and different volumes (0.1 to 0.5 ml) of both the dilution and the initial suspension were plated onto DPY (dextrose-peptone-yeast extract) plates. DPY medium was of the following composition (per liter):

| Component | Amount |
| --- | --- |
| Dextrose | 5.0 g |
| Peptone | 1.0 g |
| Yeast extract | 2.0 g |
| $NH_4OH$ | 1.0 g |
| $K_2H_2PO_4$ | 1.0 g |
| $MgSO_4.7H_2O$ | 0.5 g |
| $FeCl_3.6H_2O$ | 0.5 ml of 1% soln. |
| oxgall (dried bovine bile) | 5.0 g |

Plates were incubated at 24° C. for 3–7 days, and the growing colonies were transferred to Potato Dextrose Agar (Difco) plates. After incubating the new plates for one week at 24° C., all the cultures isolated from the sample were morphologically compared. Strains were selected for fermentation studies. One of the strains was subsequently designated MF 5672 and was used in the fermentation which produced Compound I. This culture was registered by the American Type Collection as ATCC 74157.

What is claimed is:

1. A compound of the formula

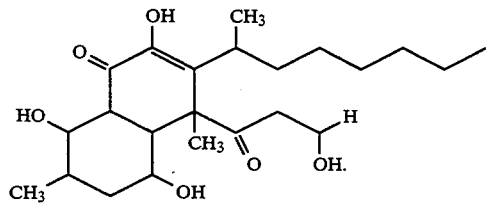

2. An antifungal composition comprising an antifungal amount of the compound of claim 1 in admixture with a biologically inert carrier.

3. A composition according to claim 2 in which the carrier is a pharmaceutically acceptable carrier.

4. A method for controlling fungal growth comprising administering to the site where growth is to be controlled, an effective amount of a compound of claim 1.

5. A method for controlling mycotic infections in patients comprising administering a therapeutically effective amount of the compound of claim 1.

6. A process for producing the compound of claim 1 which comprises aerobically cultivating a culture of Sporormiella ATCC 74157 in a nutrient medium containing assimilable sources of carbon and nitrogen and isolating said compound therefrom.

7. A method for controlling agricultural fungal infections on plants which comprises administering to the site where growth is to be controlled an effective amount of the compound of claim 1.

8. A method for treating agricultural fungal infections which comprises administering to the site where growth is to be treated an effective amount of the compound of claim 1.

9. A method for controlling Oomycete infections on plants which comprises administering to said plants an effective amount of the compound of claim 1.

10. A method for treating Oomycete infections on plants which comprises administering to said plants an effective amount of the compound of claim 1.

* * * * *